United States Patent [19]

Nakatsuka et al.

[11] Patent Number: 5,194,632
[45] Date of Patent: Mar. 16, 1993

[54] FLUORAN COMPOUND, USEFUL IN HEAT SENSITIVE RECORDING MATERIALS

[75] Inventors: Masakatsu Nakatsuka, Yokohama; Atsuo Otsuji, Kamakura; Kiyoharu Hasegawa, Yokohama; Masatoshi Takagi; Akihiro Yamaguchi, both of Kamakura, all of Japan

[73] Assignee: Mitsui Toatsu Chemicals Inc., Tokyo, Japan

[21] Appl. No.: 560,909

[22] Filed: Jul. 31, 1990

[30] Foreign Application Priority Data

Aug. 1, 1989 [JP] Japan .................. 1-197948

[51] Int. Cl.$^5$ .................. C07D 311/78; C07D 311/80
[52] U.S. Cl. .................. 549/224; 549/225; 549/226
[58] Field of Search ............... 549/224, 225, 226, 223; 503/220, 221

[56] References Cited

FOREIGN PATENT DOCUMENTS

| | | | |
|---|---|---|---|
| 48-43296 | 12/1973 | Japan . | |
| 51-23204 | 7/1976 | Japan . | |
| 54-34909 | 3/1979 | Japan . | |
| 58-096588A | 6/1983 | Japan | 549/226 |
| 60-35053 | 2/1985 | Japan . | |
| 60-141762A | 7/1985 | Japan | 549/265 |

OTHER PUBLICATIONS

Chemical Abstracts of Japan, vol. 100, No. 18, p. 603, Abstracts No. 148555p (Apr. 30, 1984).
Chemical Abstracts of Japan, vol. 96, No. 14, p. 639, Abstract No. 113538g (Apr. 5, 1982).
Chemical Abstracts of Japan, vol. 106, No. 24, p. 605, Abstract No. 205276y (Jun. 15, 1987).
Chemical Abstracts of Japan, vol. 106, No. 6, p. 91, Abstract No. 34653n (Feb. 9, 1987).
Chemical Abstracts of Japan, vol. 98, No. 22, p. 83, Abstract No. 181134p (May 30, 1983).
Chemical Abstracts of Japan, vol. 102, No. 26, p. 74, Abstract No. 222151p (Jul. 1, 1985).

*Primary Examiner*—Carolyn Elmore
*Assistant Examiner*—Shailendra Kumar
*Attorney, Agent, or Firm*—Millen, White, Zelano and Branigan

[57] ABSTRACT

Disclosed are a novel fluoran compound represented by the formula (I):

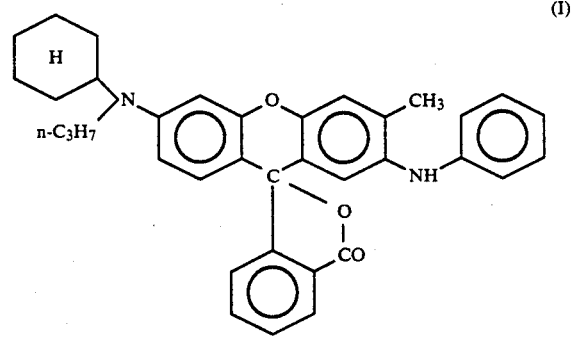

and a heat-sensitive recording paper which is obtained by using the fluoran compound as a chromogenic compound and is excellent in preserving stability.

1 Claim, 1 Drawing Sheet

FLUORAN COMPOUND, USEFUL IN HEAT SENSITIVE RECORDING MATERIALS

BACKGROUND OF THE INVENTION

1. Field of the Invention

The present invention relates to a novel fluoran compound which is useful as a chromogenic compound in a heat-sensitive recording materials, to a process for the preparation of the compound and heat-sensitive recording materials comprising said compound.

2. Description of the Prior Art

Heat-sensitive recording systems utilizing a color reaction between a colorless or pale colored electron donative compound (chromogenic compound) and an organic or inorganic electron acceptor (developer) have been widely popularized.

In the recording system, fluoran compounds have widely been used as the chromogenic compounds.

Many fluoran compounds are known in the prior art, for example those having the formulas (A), (B) and (C).

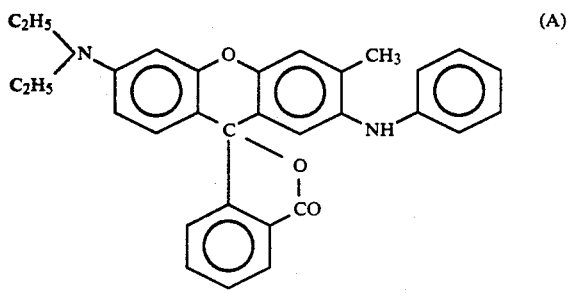

Japanese Patent Publication SHO 48-43296 (1973)

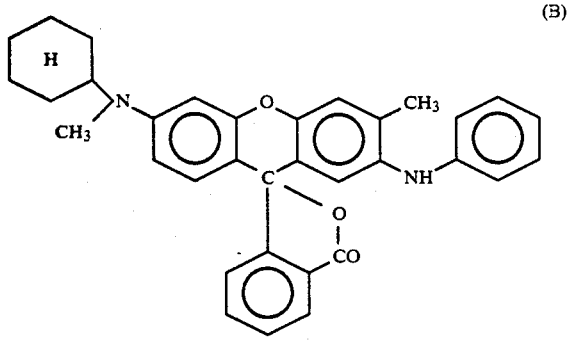

Japanese Patent Publication SHO 51-23204 (1976)

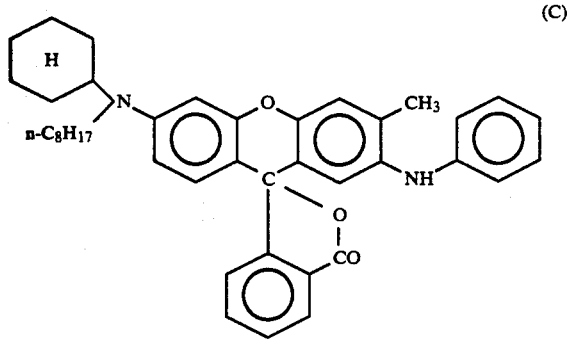

Japanese Patent Laid-Open Publication SHO 60-35053 (1985).

However, when used in a heat-sensitive recording material, the compound of the formula (A) has the defect that the compound itself colors gray to dark gray when mixed with a developer such as bisphenol A and imparts a only a gray to dark gray (soiled) color to paper when the mixture is applied to a paper.

The compound of the formula (B) or the formula (C) provides a paper having relatively high whiteness immediately after application, thereto but the coated paper has a disadvantage of becoming to gray or brown under the influence of moisture, light or heat.

The heat-sensitive recording material has recently been used indoors as in the case of facsimile paper and additionally in the open air under more severe conditions as in the case of, for example, prepaid cards such as telephone cards. Consequently, the heat-sensitive recording materials are required to further enhance preserving stability.

OBJECT OF THE INVENTION

The object of the present invention is to provide a novel fluoran compound having an excellent preserving stability as a chromogenic compound for use in the heat-sensitive recording materials, and additionally to provide a process for the preparation of a novel fluoran compound and heat-sensitive recording materials comprising a novel fluoran compound of this invention.

SUMMARY OF THE INVENTION

One aspect of the present invention relates to a novel fluoran compound represented by Formula (I):

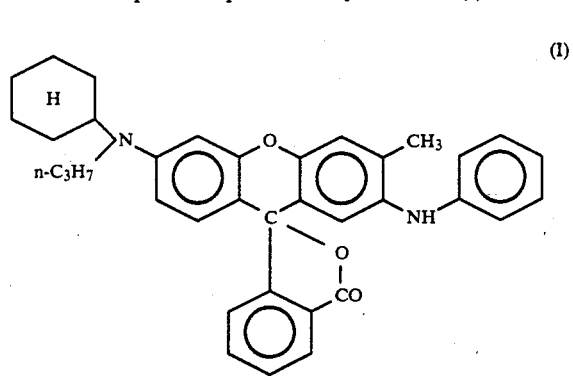

Another aspect of the present invention relates to a process for the preparation of the fluoran compound of this invention by reacting a benzoic acid derivative represented by Formula (II):

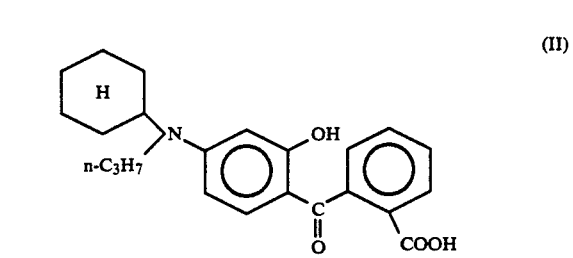

with a diphenylamine derivative represented by Formula (III):

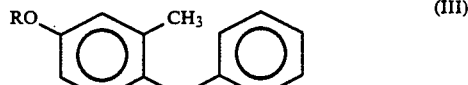

wherein R is a lower alkyl group.

A further aspect of the present invention relates to a heat-sensitive recording materials comprising the fluoran compound of this invention.

In this drawing, axis of ordinate indicates transmittance and axis of abscissa indicates wave number $(cm^{-1})$.

Figure 2:
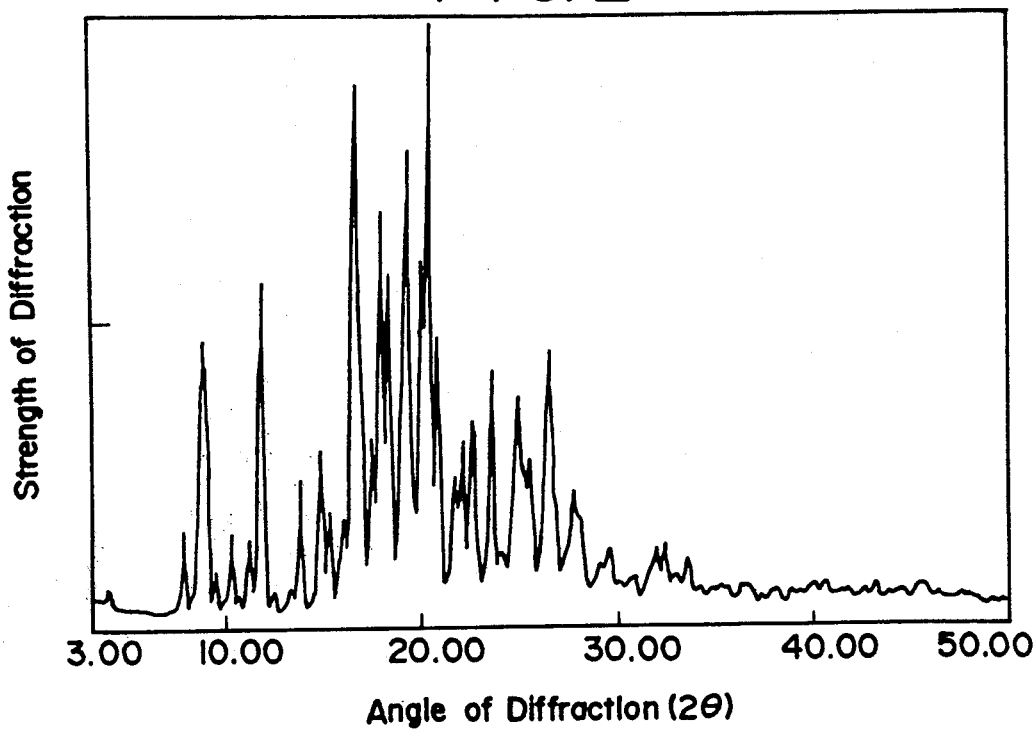

FIG. 2 illustrates an X-ray diffraction pattern of a crystal powder of the fluoran compound of Formula (I).

In this drawing, axis of ordinate indicates strength of diffraction and axis of abscissa indicates angle of diffraction ($2\theta$).

DETAILED DESCRIPTION OF THE INVENTION

The benzoic acid derivative of Formula (II) for use in the preparation of the fluoran compound of Formula (I) can be prepared, for example, by reaction of 3-N-cyclohexyl-N-n-propylaminophenol with phthalic anhydride in the absence or presence of a solvent such as benzene, toluene, xylene and tetrachloroethylene. A Lewis acid, such as zinc chloride, may also be added to the reaction.

The diphenylamine derivatives of Formula (III) have a lower alkyl group represented by R. Examples of the lower alkyl group are preferably methyl and ethyl, and methyl is preferred in particular.

The fluoran compound of Formula (I) can be prepared by reacting a benzoic acid derivative of Formula (II) with the diphenylamine derivative of Formula (III) in the presence of a dehydrating condensation agent such as concentrated sulfuric acid, a mixture of concentrated sulfuric acid and oleum, polyphosphoric acid, phosphorus pentoxide and anhydrous aluminum chloride, more preferably in concentrated sulfuric acid, and thereafter bringing the reaction mixture to an alkaline pH.

The time and temperature of the dehydrating condensation reaction is not critical and is usually carried out at 0° to 100° C. for from several hours to 100 hours. When the reaction is carried out in concentrated sulfuric acid, the preferred reaction temperature is in the range of 0° to 50° C. The reaction time depends upon the selected reaction temperature and hence the reaction is conducted for a sufficient length of time to permit the reaction to go to completion.

After the dehydrating condensation reaction is completed, the alkali treatment is usually carried out by the addition of a base, e.g., aqueous potassium hydroxide or sodium hydroxide solution, to adjust the pH to an alkaline value, e.g., 9 to 12. The treatment can be conducted in the temperature range of 0° to 100° C. The alkali treatment may also be conducted in the presence of an organic solvent other than water, for example, benzene and toluene.

When preparing a heat-sensitive recording material of the present invention, the fluoran compound of the present invention is pulverized in water to form an aqueous dispersion. The aqueous dispersion is mixed with an aqueous dispersion of pulverized developer, and binder is added to the thus obtained mixture.

Representative examples of developers which are suitable for use in the heat sensitive recording materials of the present invention include phenols such as bisphenol A, halogenated bisphenol A, alkylated bisphenol A, dihydroxyphenyl sulfone, halogenated dihydroxyphenyl sulfone, alkylated hydroxybenzoic acid esters, and hydroquinone monoethers; organic developers such as salicylic acid derivatives, salicylamide derivatives, urea derivatives, and thiourea derivatives; and inorganic developers such as acid clay, attapulgite, activated clay, aluminum chrolide and zinc bromide.

Exemplary binder used for the heat-sensitive recording material of the present invention includes polyvinyl alcohol, modified polyvinyl alcohol, methylcellulose, hydroxyethylcellulose, carboxymethylcellulose, gum arabic, salt of styrene-maleic anhydride copolymer, and isobutylene-acrylic acid-maleic anhydride copolymer.

Other additives can also be employed, exemplary other additives include fillers, such as talc, kaolin and calcium carbonate; and if necessary, also sensitizers, such as higher fatty acid amides, aromatic carboxylic acid esters, aromatic sulfonic acid esters, aromatic ethers, aralkyl ethers, aromatic hydrocarbons, aromatic substituted aliphatic hydrocarbons and other generally known sensitizers for the heat-sensitive recording materials; UV-absorbers; and defoamers.

The coating liquid obtained by the addition of the above additives can be applied to a suitable substrate such as paper, plastic sheet and resin coated paper and used as the heat-sensitive recording material. The heat-sensitive recording system of the present invention can of course be used in an organic solvent system without any problem in place of the above described aqueous dispersion system.

The fluoran compound of Formula (I) can be used singly as the chromogenic compound. Further, in order to adjust the developed hue, other chromogenic compounds such as triphenylmethanelactones, fluorans and spiropyrans can also be added depending upon the color demand.

The fluoran compound of Formula (I) has a melting point of 257° to 258° C. The melting point is extraordinarily higher than those of known compounds, for example, from 195° to 198° C. for the compound of Formula (A), from 195° to 197° C. for the compound of Formula (B), and from 124° to 126° C. of the compound for the formula (C).

The fluoran compound of Formula (I) has very low solubility in organic solvents, for example, hydrocarbons such as benzene and toluene, esters such as ethyl acetate, and ketones such as acetone.

For example, the solubility of the compound of Formula (I) was compared with known fluoran compounds of Formulas (A), (B) and (C). The results are shown in Table 1. Solubility is indicated by weight percent in toluene at 25° C.

TABLE 1

| Compound | Solubility |
|---|---|
| (I) | 0.5% or less |
| (A) | 8% |
| (B) | 5% |
| (C) | 12% |

A heat-sensitive paper having a high whiteness without a paper soiling effect can be obtained by using the compound of Formula (I) having the above properties for the heat-sensitive recording material. The paper is extremely excellent in preserving stability such as resistance to moisture and solvents. For example, when a heat-sensitive recording paper prepared by using bisphenol A as a developer and the compound of the invention of Formula (I) as a chromogenic compound is compared with the heat-sensitive recording papers prepared by using the compounds of Formulas (A), (B) or (C) on the moisture-heat resistance and oil resistance of uncolored portion, results illustrated in Table 2 are obtained.

The moisture and heat resistance test was carried out by keeping the heat-sensitive paper prepared from each compound at 60° C. for 24 hours in the relative humidity of 90% and thereafter by visually observing the soil of the paper.

The oil resistance test was carried out by bringing the heat-sensitive recording paper into contact with dioctyl phthalate and allowing to stand for a week and thereafter by visually observing the soil of the paper.

TABLE 2

| Compound | Immediately after application | Moisture and heat resistance | Oil resistance |
| --- | --- | --- | --- |
| (I) | ○ | ○ | ○ |
| (A) | △ | X | X |
| (B) | ○ | X | X |
| (C) | ○ | X | X |

Note:
○ Paper with a high whiteness without soil
△ Paper soiled to pale gray
X Paper soiled to gray The fluoran compound of Formula (I) differs from the fluoran compounds Formulas (A), (B) or (C) only in the substituent on the amino group at the 3 position of the fluoran structure. For example, the compound of Formula (I) differs from the compound of Formula (B) in the substituent on the amino group at the 3 position being n-propyl group instead of methyl group. Although, these differences in chemical structure are small, as mentioned above, the fluoran compound of Formula (I) has a very high melting point and extremely low solubility in organic solvents as compared to the fluoran compounds of Formulas (A), (B) and (C). The preserving stability of the heat-sensitive paper can be greatly improved as described above by using the fluoran compound of Formula (I) of the present invention for the heat-sensitive recording material.

As to the solubility in organic solvents, although the solubility of a compound is generally thought to increase in organic solvents, in particular hydrocarbon solvents, by increasing the length of an alkyl chain e.g., by replacing a methyl group by a n-propyl group. Surprisingly the fluoran compound of the formula (I) of the present invention has much lower solubility in toluene as compared with the fluoran compound of Formula (B).

As an example of the effect of such replacement by a longer chain, the compound of Formula (D):

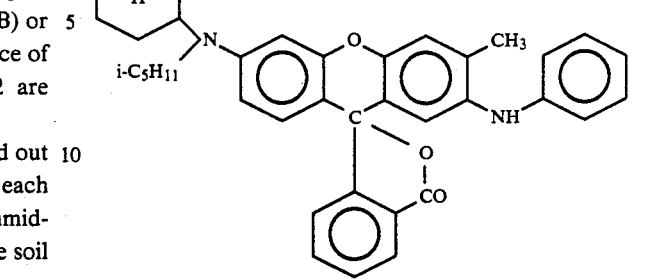

which differs from methylamino substituted compound at the 3 position of the Formula (B) by an isoamylamino group, has high solubility in organic solvents, in particular hydrocarbons such as toluene see Japanese Patent Laid-Open Publications SHO 54-34909 (1979).

However, the fluoran compound of Formula (I) which has a n-propyl group on the amino group, the a conventionally unknown characteristic of a solubility in toluene which is extremely low as compared with the fluoran compound of Formula (B). Thus, a heat-sensitive recording paper having an excellent preserving stability can be provided by using the fluoran compound of the invention as the chromogenic compound.

The present invention will hereinafter be illustrated further in detail by way of examples. However, it is to be understood that the invention is not intended to be limited to the specific embodiments.

EXAMPLE 1

Preparation of the compound of Formula (I)

Figure 1:
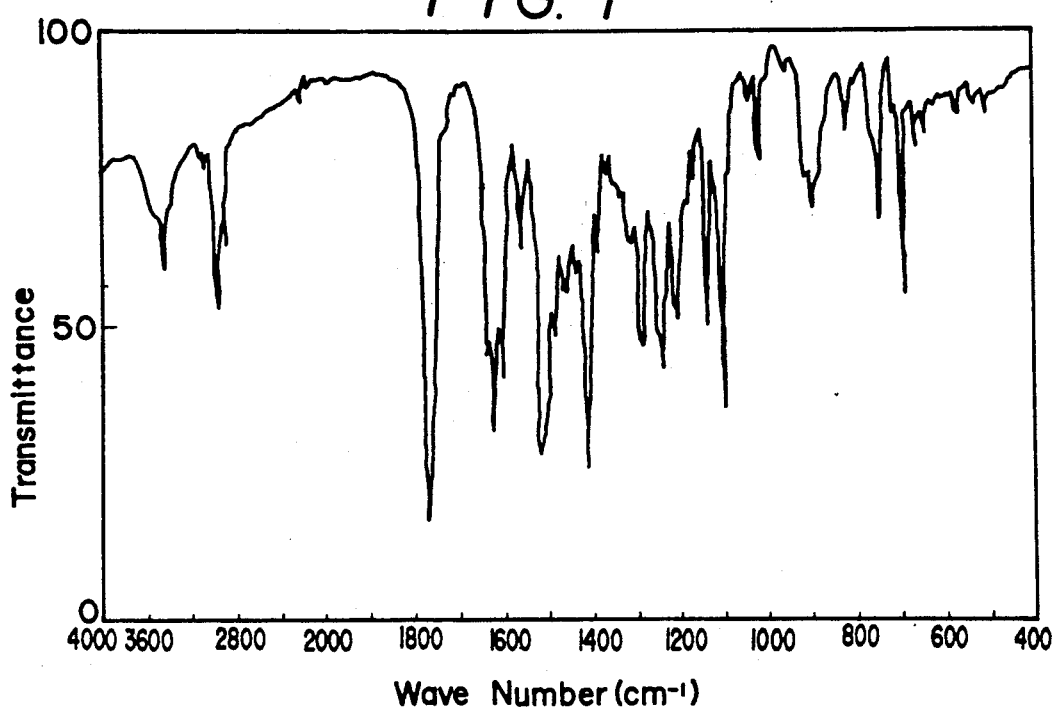
FIG. 1 illustrates an IR absorption spectrum (KBr tablet) of the fluoran compound of Formula (I).

After dissolving 20 g of 2-(4'-N-cyclohexyl-N-n-propylamino-2'-hydroxybenzoyl)benzoic acid (II), in 100 ml of concentrated sulfuric acid at 10° C., 11 g of 4-methoxy-2-methyl-diphenylamine (III) wherein R is methyl was added at the same temperature and stirred at 10° to 25° C. for 48 hours. The reaction mixture was poured into 600 ml ice water. The precipitated solid was collected, washed with water and added to 500 ml of an 10% aqueous sodium hydroxide solution. The mixture was stirred at 60° to 70° C. for 2 hours and filtered. The solid obtained was washed with water, with 100 ml of isopropanol and then washed twice with toluene. Thus, 20 g of the desired 3-N-cyclohexyl-N-n-propylamino-6-methyl-7-anilinofluoran was obtained as almost colorless crystals. The yield was 69%. Melting point was 257° to 258° C. The IR absorption spectrum (KBr tablet) is illustrated in FIG. 1. The X-ray diffraction diagram of crystal powder of the compound is illustrated in FIG. 2.

EXAMPLE 2

Preparation of heat-sensitive recording paper using the compound of Formula (I)

A mixture composed of 10 g of 3-N-cyclohexyl-N-n-propylamino-6-methyl-7-anilinofluoran, 5 g of a 10% aqueous polyvinyl alcohol solution and 37.5 g of water was pulverized to a particle size of 3μ with a sand mill. Separately, bisphenol A was dispersed in a similar manner to obtain a 38% developer dispersion. To 65.8 g of the developer dispersion, 50 g of the above aqueous dispersion of 3-N-cyclohexyl-N-n-propylamino-6-methyl-7-anilinofluoran, 18.3 g of a 60% aqueous dispersion of precipitated calcium carbonate, 88 g of 10% aqueous polyvinyl alcohol solution and 51.9 g of water were added and mixed.

The mixture thus obtained was coated onto a white free paper, using a wire rod No. 10, and allowed to dry at room temperature to obtain a heat-sensitive recording paper having a very high whiteness without soil. The heat-sensitive recording paper thus obtained very quickly developed a slightly reddish black color by heating. The developed image had good preserving properties such as heat resistance, moisture-heat resistance, and light resistance.

The heat-sensitive recording paper was allowed to stand at 60° C. for 24 hours in 90% relative humidity. After the test, the paper retained the whiteness obtained immediately after application and no soil in appearance was found at all. The applied surface of the heat-sensitive recording paper was brought into contact with dioctyl phthalate and stored for a week. After the test, no soil of the paper was observed at all. Results are illustrated in Table 2.

COMPARATIVE EXAMPLE

Heat-sensitive recording papers were prepared by carrying out the same procedures as described in Example 2 except that 3-N-cyclohexyl-N-n-propylamino-6-methyl-7-anilinofluoran was replaced by 3-N,N-diethylamino-6-methyl-7-anilinofluoran, i.e., the compound of Formula (A), 3-N-cyclohexyl-N-methylamino-6-methyl-7-anilinofluoran, i.e., the compound of Formula (B), and 3-N-cyclohexyl-N-octylamino-6-methyl-7-anilinofluoran, i.e., the compound of the formula (C), respectively.

The moisture and heat resistance test and the oil resistance test were conducted. The results are illustrated in Table 2.

The coated surface of the heat-sensitive recording paper prepared using the compound of Formula (A) was soiled to a pale gray shade immediately after coating.

We claim:

1. A fluoran compound represented by the formula (I):

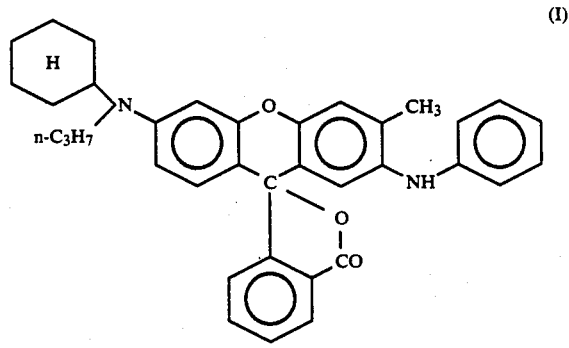

* * * * *